(12) United States Patent
MacFarland et al.

(10) Patent No.: US 10,794,882 B2
(45) Date of Patent: Oct. 6, 2020

(54) AQUEOUS COLORIMETRIC FLUORIDE DETECTION

(71) Applicant: Hach Company, Loveland, CO (US)

(72) Inventors: Darren Kent MacFarland, Windsor, CO (US); Angella Nicholle Greenawalt, Fort Collins, CO (US)

(73) Assignee: HACH COMPANY, Loveland, CO (US)

(*) Notice: Subject to any disclaimer, the term of this patent is extended or adjusted under 35 U.S.C. 154(b) by 285 days.

(21) Appl. No.: 15/951,927

(22) Filed: Apr. 12, 2018

(65) Prior Publication Data

US 2019/0317064 A1    Oct. 17, 2019

(51) Int. Cl.
| | | |
|---|---|---|
| *G01N 31/22* | (2006.01) | |
| *G01N 33/18* | (2006.01) | |
| *G01N 21/78* | (2006.01) | |

(52) U.S. Cl.
CPC .............. *G01N 31/22* (2013.01); *G01N 21/78* (2013.01); *G01N 33/182* (2013.01)

(58) Field of Classification Search
CPC ...... G01N 31/22; G01N 33/18; G01N 33/182; G01N 21/77; G01N 21/78; Y10T 436/145555; Y10T 436/19; Y10T 436/193333
USPC ................. 436/124, 125, 96, 72, 164, 166
See application file for complete search history.

(56) References Cited

U.S. PATENT DOCUMENTS 7,396,691 B2 *  7/2008  Ezan ...................... G01N 33/84
                                                                  423/325

OTHER PUBLICATIONS

Yang et al. RSC Advances, vol. 3, 2013, pp. 20171-20178.*

* cited by examiner

*Primary Examiner* — Maureen Wallenhorst
(74) *Attorney, Agent, or Firm* — Ference & Associates LLC

(57) ABSTRACT

An embodiment provides a method for measuring fluoride concentration in an aqueous solution, including: preparing a polyethylene glycol (PEG) monomethyl ether to produce an ester; reacting the ester in the presence of ammoniated tetrahydrofuran to produce an amino polyethylene glycol; placing, in a solution comprising a benzaldehyde species with a phenol functional group and a carboxylic acid functional group, a 2,3,3-trimethylindolenine derivative to produce a hemicyanine with a phenol functional group and a carboxylic acid functional group; combining, in a polar aprotic solvent, the hemicyanine with the phenol functional group and carboxylic acid functional group with a 1,1-carbonyldiimidazole (CDI) and adding the amino-PEG to produce a hemicyanine-PEG; and creating a fluoride sensitive hemicyanine species by reacting the hemicyanine-PEG that contains a phenol functional group with a $SiR_3$ species. Other embodiments are described and claimed.

9 Claims, 10 Drawing Sheets

AQUEOUS COLORIMETRIC FLUORIDE DETECTION

BACKGROUND

The measurement of fluoride in drinking water is an important task for water treatment facilities. Most municipal water facilities introduce a controlled amount of fluoride into drinking water. One benefit to this introduction of fluoride is that when the fluoride is ingested it slows the rate of tooth enamel demineralization and increases the rate of remineralization. This process reduces the incidence of tooth cavities in the population served by fluoridated water. However, high concentrations of fluoride can be detrimental. For example, if the fluoride concentration is too high, dental fluorosis may occur. Additionally, the facility is wasting resources by the addition of too much fluoride. On the other hand, if the fluoride concentration is too low, the prevention of tooth cavities suffers. Therefore, it is desired to closely monitor the level of fluoride in drinking water to achieve a desired concentration of fluoride, and to ensure compliance with regulations.

There are a number of methods to measure fluoride in drinking water. These include the SPADNS and ion selective electrode techniques. SPADNS requires the preparation of a blank sample vial, and because the chemistry involves the bleaching of a dye, differing styles of measurement may lead to inaccurate results. The ion selective technique requires the addition of an ionic strength adjustment buffer, and the equilibrium time for low levels of fluoride that are not within a linear range may be sensitive to sample movement and temperature leading to inaccurate results.

BRIEF SUMMARY

One embodiment provides a method for measuring fluoride concentration in an aqueous solution, comprising: preparing a polyethylene glycol (PEG) monomethyl ether to produce an ester; reacting the ester in the presence of ammoniated tetrahydrofuran to produce an amino polyethylene glycol; placing, in a solution comprising a benzaldehyde species with a phenol functional group and a carboxylic acid functional group, a 1,2,3,3-tetramethyl-3H-indolium iodide to produce a hemicyanine with a phenol function group and a carboxylic acid functional group; combining, in a polar aprotic solvent, the hemicyanine with a phenol and carboxylic acid functional group with a 1,1-carbonlydiimidazole (CDI) and adding the amino-PEG to produce a hemicyanine-PEG; and creating a fluoride sensitive hemicyanine species by reacting the hemicyanine-PEG with a halogenated $SiR_3$ species.

Another embodiment provides a method for measuring fluoride concentration in an aqueous solution, comprising: synthesizing a $SiR_3$ water-soluble species, wherein the water-soluble species is selected from the group consisting of: phenol or naphthol; placing, into an aqueous solution, the $SiR_3$ water-soluble species, wherein fluoride contained within the aqueous solution deprotects the water-soluble species; and producing a quantity of azo dye by reacting, within a solution, the deprotected water-soluble species with a diazonium salt, wherein the quantity of azo dye is proportional to an amount of aqueous fluoride within the aqueous solution.

A further embodiment provides a method for measuring fluoride concentration in an aqueous solution, comprising: producing a $SiR_3$ monoprotected catechol containing a benzaldehyde group by reacting a catechol containing a benzaldehyde group with a $SiR_3$ protecting group; placing, into an aqueous solution, the monoprotected catechol, wherein fluoride contained within the aqueous solution deprotects the monoprotected catechol creating a deprotected species; and producing a quantity of a water-soluble hemicyanine by reacting the deprotected species with a 1,2,3,3-tetramethyl-3H-indolium iodide species, wherein the produced quantity of water-soluble hemicyanine is proportional to an amount of aqueous fluoride in the aqueous solution.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
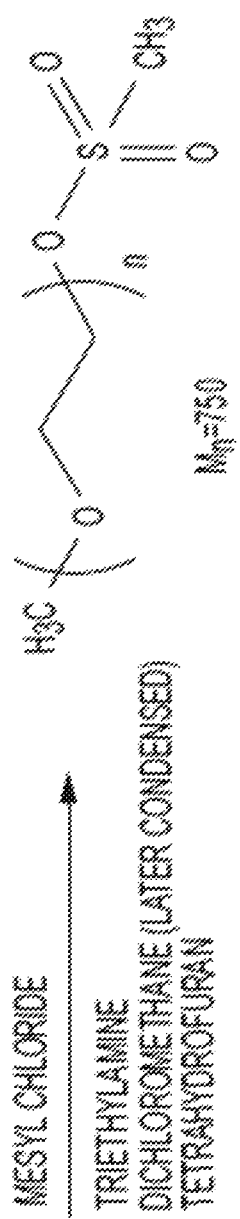
FIG. 1 illustrates a synthesis scheme of an embodiment.
Figure 1:
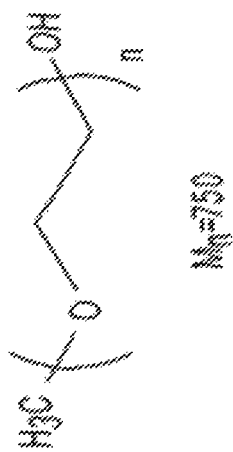

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Colorimetric and fluoride ion selective electrode methods are commonly used to measure fluoride levels. A common colorimetric method uses sulfanilic acid azochromotrope, 1,8-Dihydroxy-2-(4-sulfophenylazo)naphthalene-3,6-disulfonic acid trisodium salt, 2-(4-Sulfophenylazo)-1,8-dihydroxy-3,6-naphthalene disulfonic acid trisodium salt, 2-(4-Sulfophenylazo)chromotropic acid trisodium salt, or sodium 1-(parasulphophenylazo)-1,8-dihydroxy-3,6-naphthalene disulfate. These colorimetric methods are based upon the reaction between fluoride and a dark red zirconium dye to form a colorless complex anion. These methods result in a bleaching of the red color in an amount proportional to the fluoride concentration. For example, higher fluoride concentrations react with more of the zirconium dye and the solution turns a lighter color. The resulting color from the colorimetric reaction may be determined photometrically, for example, using a spectrophotometer. The amount of fluoride may be determined by comparison to a similarly prepared blank vial. The absorbance of the sample reacted vial must be compared to the absorbance of the unreacted blank vial to determine the fluoride concentration of the sample reacted vial.

However, the current fluoride testing methods have limitations which are overcome by the methods and techniques as described in more detail herein. One limitation of the current techniques is that they use a bleaching chemistry not favorable to some uses and measurement systems. Additionally, the traditional colorimetric methods require the preparation of a separate "blank" vial. The extra step of preparing a blank vial can introduce error to the measurement based upon individual human techniques in preparing the blank. Also, since the traditional colorimetric technique involves the bleaching of a dye, the time for preparation and time a measurement is taken, can introduce variability in the a sample reading. Additionally, because the techniques include bleaching of a dye, difficulty may arise because there may not be the same volume of starting colorimetric dye in both the blank and sample vial, thereby introducing error into the determination of the amount of fluoride found in the sample. This error may result in a false positive or false negative result.

The ion selective electrode may also have disadvantages. The ion selective electrode requires the addition of an ionic strength adjustment buffer. Measurements may be affected by the omission or addition of this buffer and it requires an additional preparation step. Also, the equilibrium time for low parts per billion (ppb) levels of fluoride is long and sensitive to both sample movement and temperature, which can in turn, lead to inaccurate results.

Accordingly, an embodiment includes generation of a hemicyanine dye that is used to detect aqueous fluoride in a sample. In an embodiment, a reaction causes the generation or formation of the hemicyanine dye. In an embodiment, a reaction causes an unmasking or deprotection of the hemicyanine dye which adds color to the sample. The color of the hemicyanine dye deepens or becomes greater and is directly proportional to a higher concentration of aqueous fluoride. If fluoride is present, the fluoride will deprotect the phenolic species, that also has a benzaldehyde functional group, which allows reaction with 1,2,3,3-Tetramethyl-3H-indolium iodide or a derivative of the species. If fluoride is not present, then the protected starting phenolic/benzaldehyde species does not react/deprotect, and no hemicyanine is produced, therefore no color is produced. Thus, the hemicyanine, which results in the color, may only be generated in the presence of fluoride.

Additionally, the dye is water-soluble. The water solubility arises from a polyethylene glycol (PEG) chain on the species. The water solubility may be a result of the R-groups present on the selected starting phenol/benzaldehyde. Alternatively, 1,2,3,3-Tetramethyl-3H-indolium iodide or a derivative, modified through a reaction with 1,3-propanesultone, may make the final hemicyanine water-soluble on its own. A reaction between fluoride and the O—Si bond drives the color generation. The hemicyanine may offer a lower toxicity method than traditional colorimetric techniques since heavy metals are not used. For example, arsenic is also present in some traditional colorimetric techniques and is used as a masking agent for certain interfering species. Other colorimetric techniques have removed the arsenic from the reactions, but still contain other heavy metals.

In an embodiment, a silane protected hemicyanine species reacts with fluoride in an aqueous environment to produce a change in color easily detectable by photometric techniques. The absorbance at a desired measurement wavelength increases in a linear fashion with respect to increasing fluoride concentrations over a certain range. This is in contrast to traditional colorimetric techniques in which the initial measurement of the colorimetric dye within the sample may be difficult because the fluoride in the sample begins to react immediately. In other words, comparing the decrease in absorbance of a reacted sample to that of a blank vial may only be accurate to a certain degree. The samples can be prepared such that any background absorbance from the reagents may be subtracted from the final measurement. Thus, both a blank and fluoride sample vial may be measured prior to addition of sample.

Additionally, an embodiment overcomes the need for co-solvents through the use of a PEG (polyethylene glycol) chain and a charged dye or a charged dye through addition of R-groups such that the embodiment has sufficient water solubility in pure water. Therefore, the use of a surfactant is unnecessary, such as hexadecyltrimethylammonium bromide (CTAB).

An embodiment comprises hemicyanine dye which provides a color to the sample and is visible on the visible spectrum. For example, the hemicyanine dye may have an absorbance in the red portion of the color spectrum. For example, an absorbance in the 500-530 nm range. Alternatively to the red color, an embodiment may alter the chemistry of the dye to any wavelength in the visible (such as yellow or green), ultraviolet (UV), or infrared spectrums using techniques known in chemistry.

An embodiment comprises a bulky $SiR_3$ group which minimizes non-fluoride hydrolysis. The modification of a chromophore by the addition of a $SiR_3$ group through a phenol group can create fluoride sensitivity if the "free" and silylated phenol species have different absorbance characteristics. The oxygen-silicon bond is subject to selective cleavage by fluoride anion. The same oxygen-silicon bond also hydrolyzes if the silyl group is small, or at extreme pH values. A $SiR_3$ group such as tert-butyldiphenylsilyl chloride or any other similar $SiR_3$ group may be used. Control of the sample pH contributes to stability of the sample. For example, a TRIS (tris-(hydroxymethyl)-aminomethane) buffer or other buffers may be used. The rate of hydrolysis may be dependent upon the $SiR_3$ group chosen. Stability of the $SiR_3$ groups may decrease at extreme pH values, but a neutral pH (i.e., of or about 7) may not be required. In an embodiment, a pH study may be performed to determine an effective pH for long term storage. The material may also be stored in a solvent such as 2-propanol to maximize stability until the reaction with an aqueous sample occurs.

In an embodiment reaction of fluoride with the O—Si bond produces a colorless F—SiR$_3$ species and regenerates the original O—H bond, which regenerates the chromophore. An embodiment of the chromophore gives a measurable absorbance directly proportional to the concentration of fluoride in solution at the specified measurement wavelength.

Some current fluoride tests use a bleaching chemistry. In other words, the color dissipates over time in the presence of fluoride, which may or may not become colorless. The hemicyanine dye disclosed herein starts with a solution that does not exhibit a significant absorbance at the desired measurement wavelength. The absorbance at the desired measurement wavelength, or over a certain wavelength range, increases when fluoride is present in solution.

An embodiment in which the solution turns from colorless to a color has advantages. Accordingly, an embodiment is able to get an initial measurement because the measurement is colorless, or does not exhibit a significant absorbance at the desired measurement wavelength. During the reaction, the sample turns a color which can then be measured. In other words, an embodiment goes from colorless to some degree of color. For example, colorless to pink to red over time. Further embodiments include the possibility of other colors such as yellow, green, or any other color measurable by laboratory apparatus. The absorbance can be translated to the concentration of fluoride in solution. In an embodiment, this relationship is 1:1, however the absorbance may be different for other species. Therefore, the techniques and methods as described herein may be used with current technologies.

As stated above, different colors may be produced using different chemicals. Different fluoride detecting species may exhibit an absorbance at different wavelengths. In an embodiment, red in the 500-530 nm range may be used. Red provides an easy transition, is detectable, and obtains the accuracy to measure small changes in fluoride concentration. The absorbance measured at the desired wavelength increases with increasing concentrations of fluoride. The absorbance may be directly proportional to the concentration of fluoride over a certain range.

Figure 5:
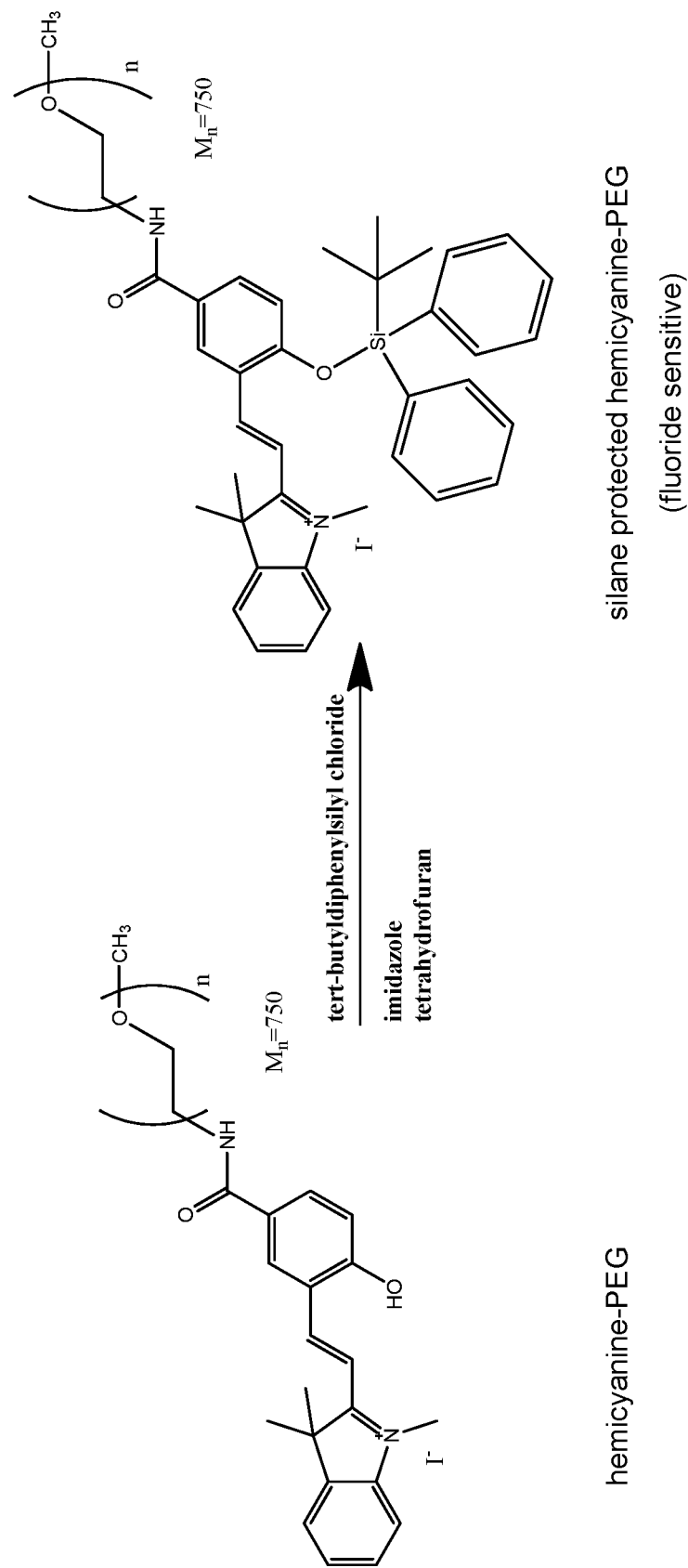
FIG. 5 illustrates a synthesis scheme of an embodiment.

In an embodiment, the use of the red portion of the spectrum for the fluoride sensitive dye allows higher usability. For example, many commercially available absorbance instruments utilize red light emitting diodes (LED) in the 500-530 nm range. A measurement may be performed by numerous platforms, such as a spectrophotometer. In an embodiment, a colored species is protected with a silane protecting group. The reaction, for example, as shown in FIG. 5, as described in more detail below, abstracts a proton from phenol which mutes the color or shifts color, such that the color is not at the wavelength of interest. If a base such as imidazole is present, the proton on the phenol may be abstracted and a selected silyl chloride protecting group reacts by loss of the chloride which forms HCl which further reacts with the imidazole to form an insoluble (in tetrahydrofuran) imidazolium hydrochloride salt. The oxygen and silicon form a bond that may be cleaved specifically by fluoride. Extreme pH or large concentrations of cyanide may also cleave this bond. Then, when fluoride is present in solution, it reacts with the oxygen silicon bond and the phenol is regenerated, thus regenerating the colored species.

In one embodiment, rather than requiring an initial masking of the colored species, the reaction itself generates a colored species. In other words, a possibly uncolored or low absorbance at a desired wavelength of measurement reagent may be introduced into the sample, and an embodiment provides a chemical reaction where the colored species is generated during the reaction as a result of the presence of fluoride. Such a technique may prevent an inaccurate measurement due to partial masking of the colored species at the onset or unmasking of the colored species caused by something other than the fluoride in the sample.

Embodiment 1

Referring now to FIG. 1, an embodiment promotes water solubility for detection of fluoride in an aqueous environment. An embodiment, utilizes polyethylene glycol (PEG) monomethyl ether reacted with a solution to prepare an ester such as mesylate, tosylate, or the like. PEG is an oligomer, and commonly used in the field of chemistry to enhance the water solubility of a compound. PEG may be prepared by the polymerization of ethylene oxide. Alternatively, PEG or the PEG-ester may also be used from a commercial source. The size of the PEG structure is often expressed in terms of a weight average molecular weight (MW) or number average molecular weight ($M_n$). An embodiment, uses PEG with a $M_n$ value of 750. Additionally, PEG with $M_n$ values of any value may be used as well. An embodiment may contain mesyl chloride, triethylamine, dichloromethane, and/or tetrahydrofuran included in the reaction of PEG to the ester.

Figure 2:
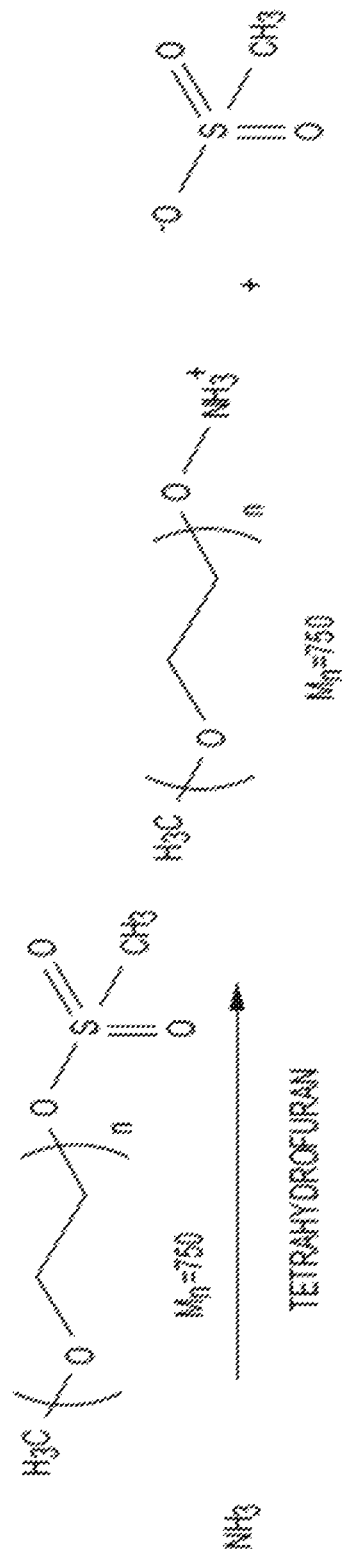
FIG. 2 illustrates a synthesis scheme of an embodiment.

Referring to FIG. 2, an amino PEG species is generated. An embodiment reacts a mesylate, tosylate, or the like species in the presence of ammonia (NH$_3$) in the form of ammoniated tetrahydrofuran (THF). The reaction creates a good leaving group as a result of the mesylate/tosylate, and generates an amino PEG. An embodiment of the amino PEG has a $M_n$ value of 750. Alternatively, an amino PEG may have any $M_n$ value.

Figure 3:
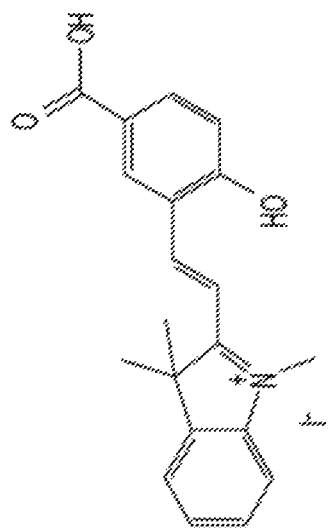
FIG. 3 illustrates a synthesis scheme of an embodiment.
Figure 3:
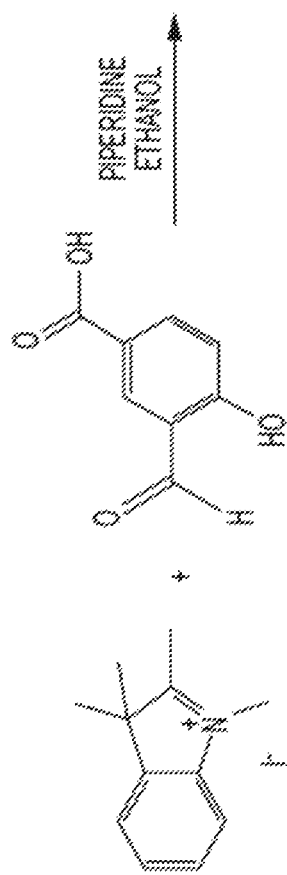

Referring to FIG. 3 a colorimetric species is generated. In an embodiment, the colorimetric species is a hemicyanine. In an embodiment, the reaction starts with 1,2,3,3-Tetramethyl-3H-indolium iodide, reacting with any aromatic benzaldehyde. The reaction between the 1,2,3,3-Tetramethyl-3H-indolium iodide and a benzaldehyde in the presence of a base (piperidine) in a polar protic solvent (ethanol) may produce a sufficiently water-soluble hemicyanine. Solubility decreases upon protection of the phenol with the silane protection group. The benzaldehyde may contain a carboxylic acid and a phenol. The carboxylic acid participates in the reaction with the amino-PEG to increase the solubility of a silylated species. The phenol participates in the reaction with the silyl chloride species to generate the fluoride sensitive portion of the dye.

Figure 4:
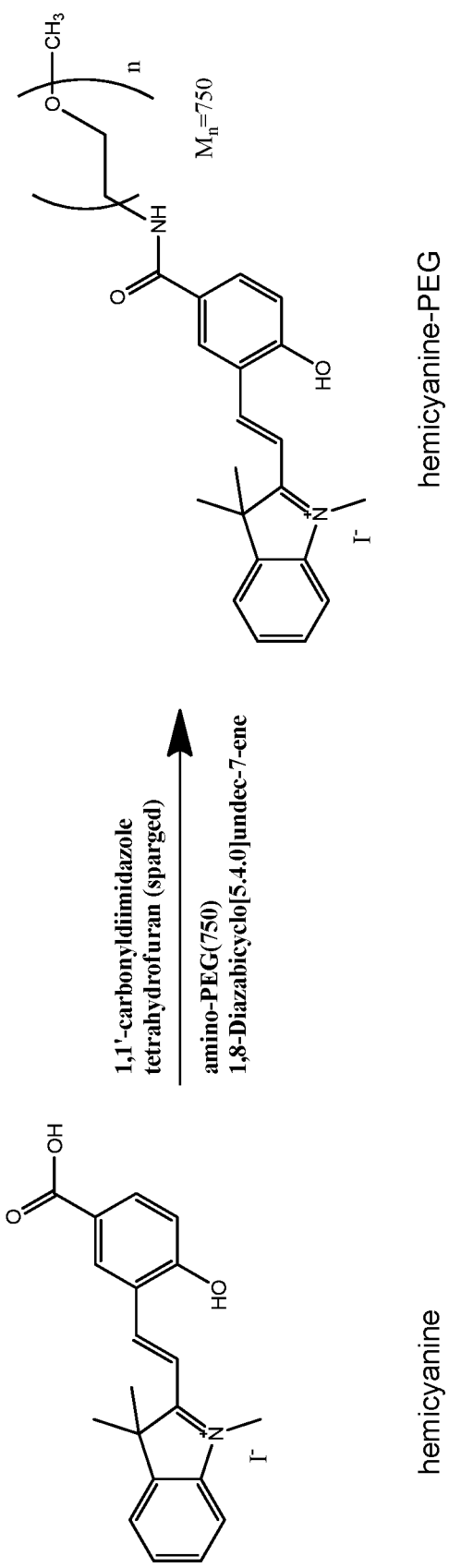
FIG. 4 illustrates a synthesis scheme of an embodiment.

Referring to FIG. 4, in an embodiment the resulting species from FIG. 3 may be reacted with the resulting species from FIG. 2. This reaction takes place when the hemicyanine (FIG. 3 product) reacts with 1,1-carbonyldiimidazole (CDI) in a oxygen-free polar aprotic solvent (THF) and is subsequently reacted with the amino-PEG (FIG. 2 product) in the presence of a non-nucleophilic base such as 1,8-Diazabicyclo[5.4.0]undec-7-ene (DBU). The reaction in FIG. 4, hemicyanine-PEG results in a water-soluble hemicyanine. The conjugation of the molecule results in a colored species that exhibits an absorbance in the visible spectrum.

A protecting group is present. A protecting group may be placed on a molecule by way of a specific functional group. A protecting group may protect a group on the molecule such it survives the reagents or chemical reactants in a multistep synthesis scheme. Different protecting groups are required for different functional groups. Since we are protecting phenol, silyl ethers may be appropriate. Accordingly, in an embodiment, this protecting group may be a silane protecting group. The product from FIG. 4 is further reacted with a silane protecting group. The result is a water-soluble silane protected Hemicyanine-PEG species. This type of protecting group is specific for the reaction with fluoride, only derivatives of the silyl halide protecting groups may be used.

This reaction interferes with the conjugation of the dye which results in a suppression of the initial color overall, or a shift of the absorbance that the dye displays. This suppression or muting may do one of two things. The muting may shift the wavelength to have an absorbance different from that of the protonated species. Alternatively, the muting may mute color at the same wavelength.

Referring to FIG. 5, a silane protected hemicyanine-PEG species is generated; a fluoride reactive species. The O—Si bond is selective for fluoride. When a base is present, the proton on the phenol is abstracted and the chosen silyl chloride protecting group reacts by loss of the chloride which forms HCl which further reacts with imidazole to form an insoluble (in THF) imidazolium hydrochloride salt. The oxygen and silicon form a bond that is cleaved specifically by fluoride. Extreme pH or large concentrations of cyanide can also cleave this bond, but if this much cyanide is present in the sample, the amount of fluoride may be immaterial.

In an embodiment, the concentration of aqueous fluoride may be determined using a portable analyzer, for example, a portable parallel analyzer (PPA) (Hach® SL1000), which can be a handheld unit that can be used to measure or analyze different elements in an aqueous sample. As used with the system described herein, the portable analyzer testing may perform colorimetric tests in the field, which may reduce the testing time. The portable analyzer may also help mitigate human introduced variability to testing methods through the use of automation of the process and control of environmental parameters such as temperature or the like.

Some portable analyzers use a sample vial or cuvette that is inserted into the portable analyzer. In one embodiment, the vial or cuvette may contain all of the necessary reagents to perform the testing chemistry. Alternatively, a powder pillow containing necessary reagents may be added to a cuvette. Therefore, in an embodiment, the silane protected hemicyanine-PEG species and associated reagents, such as buffers or the like, are located within the cuvette. The cuvette may be inserted into the portable analyzer. The fluoride in the aqueous sample may react with the silane protected hemicyanine-PEG species, and cleave the O—Si bond. The cleaving of the O—Si bond results in the release of the hemicyanine-PEG species which will yield a color change in the sample. A sensor in the portable analyzer capable of detecting a wavelength in the visible spectrum of the sample may be used to determine the fluoride concentration.

In an embodiment, the fluoride sensitive hemicyanine may be used in an on-line analyzer using a colorimetric method. In an embodiment the analyzer may be capable of the detection of fluoride in an aqueous sample. Alternatively or additionally, fluoride concentration measurement may be at periodic intervals set by the user or preprogrammed frequencies in the device. Measurement of fluoride by a device allows for real time data with very little human involvement in the measurement process. Cleaning of the colorimetric chamber may be required at an unspecified time interval. A programmed calibration curve may be entered into the device.

To determine the amount of fluoride in the sample, the resulting measurement can be determined based upon a calibration curve. The calibration curve is built based on the hemicyanine-PEG species and is linear for a predetermined range. The absorbance of the sample can be used to determine the concentration of fluoride in solution. In other words, a higher fluoride concentration results in a greater absorbance. Since the reaction is not a bleaching chemistry, there is decreased error resulting from the time to mix an aqueous sample with the chromophore because there is no need to quickly obtain a measurement before the bleaching begins to occur. Calibration may be verified periodically to ensure proper compliance with regulatory agency requirements.

The free ion analyzer may contain a colorimetric cell. A colorimetric cell may contain an aqueous sample, a hemicyanine, and associated reagents. An analyzer may contain one or more bottles of reagents which contain necessary reagents such as, but not limited to, the hemicyanine, buffers, or any reagent that may not be premixed before the sampling process. The regents contained in the one or more bottles may be pump fed or gravity fed. The flow of the reagents may be metered to ensure proper volume delivery to the colorimetric cell. The aqueous sample may be fed through a pressured inlet, a vessel, or the like. The aqueous sample may be introduced into the colorimetric chamber by a pump or gravity fed. The sampling device may be in series or parallel to an aqueous flow. The device may have a system to endure proper mixing of the aqueous sample, a hemicyanine, and related reagents.

The fluoride concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of fluoride concentration outside acceptable levels. An embodiment may use a system to shut down water output or shunt water from sources with unacceptable levels of fluoride. For example, a fluoride measuring device may use a relay coupled to an electrically actuated valve, or the like.

In an embodiment the silane protected hemicyanine-PEG species may be used to determine fluoride concentration using a simple dropper method. The dropper may be a dropper of any size such as a medicine dropper style, micropipette, or the like. A silane hemicyanine-PEG species and related reagents may be added to a known volume of an aqueous sample. The resulting color changing mixture may then be placed in a device to measure the absorbance, for example a spectrophotometer. Alternatively, the resulting color change of the aqueous sample may be compared to a card of color bands to determine fluoride concentration correlated to the color change from the presence of fluoride.

An embodiment may use a test strip. The test strip may contain the silane protected hemicyanine-PEG species and related reagents. The test strip may be dipped into the sample solution, or a known volume of sample solution may be placed on the test strip. The test strip may then be placed in a device to measure the color change.

In an embodiment a powder pillow may be used. The powder pillow contains premeasured amounts of the silane protected hemicyanine-PEG species and related reagents. The powder pillow may then be added to a volume of sample solution to measure aqueous fluoride concentration through a color change. The powder pillow may be a sachet opened by the user and the contents emptied into the sample. Alternatively, a powder pillow may have a dissolvable, non-reactive coating, allowing a user to place the powder pillow into the sample. The resulting color may then be placed in a device to measure the color change. Alternatively, the resulting color change of the aqueous sample may be compared to a card of color bands to determine fluoride concentration correlated to the color change from the presence of fluoride.

The hemicyanine species for the detection of aqueous fluoride detection may have an advantage over current techniques because the hemicyanine species may have lower toxicity than chemicals used in traditional techniques. Traditionally methods for fluoride detection may utilize heavy metals. For example, one traditional colorimetric technique may use arsenic. As another example, one traditional colorimetric technique may use zirconium. Although zirconium is naturally occurring and present in the human body, even short-term exposure to the powder may cause skin irritation. Regulatory agencies have placed a limit on the amount of daily exposure for humans. Additionally, the reaction does not require a surfactant or CTAB additive. Thus, the techniques as described herein provide an environmentally safer or "green" benefit.

The hemicyanine reaction may be performed at a neutral pH. The neutral pH and lack of heavy metal may introduce fewer limitations on disposal of the reaction solution or even the Hach Chemkey®. This would be due to possible lower toxicology since heavy metal and pH are not a concern. An added benefit is the safety of workers, cheaper disposal, and less monitoring of potentially harmful attributes.

Embodiment 2

Figure 6:
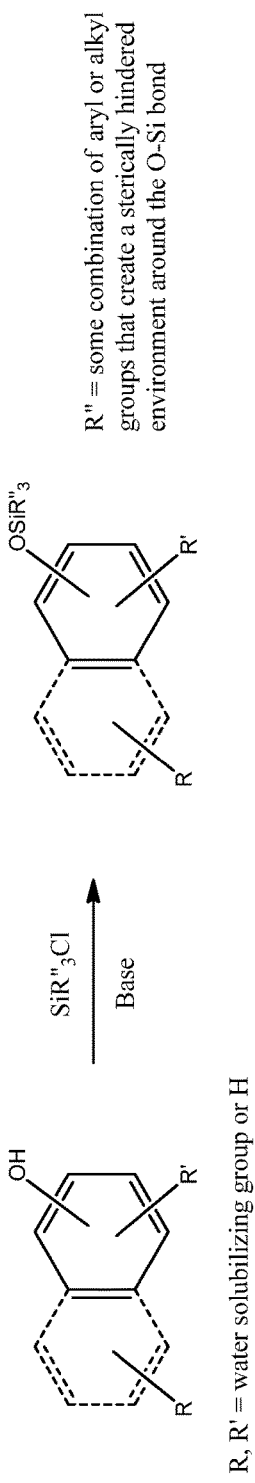
FIG. 6 illustrates a synthesis and test scheme of an embodiment.
Figure 6:
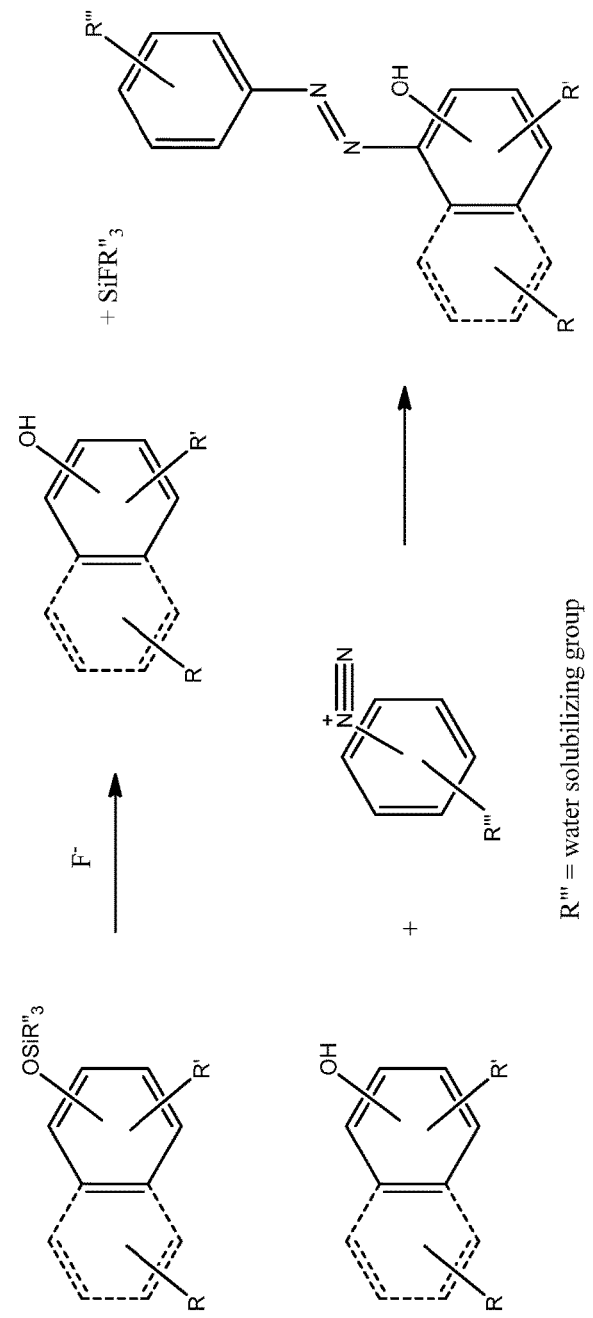

Referring to FIG. 6, an embodiment provides a technique for generation of the colored species through the reaction, rather than unmasking of the colored species as discussed above. Accordingly, FIG. 6 illustrates a synthesis and test scheme of a colorimetric dye for aqueous fluoride detection. In an embodiment, a test using a diazotization reaction may require the use of a silicon-protected phenolic species with a $SiR_3$ group. Aqueous fluoride may specifically cleave an O—Si bond. A cleavage of the O—Si bond may regenerate a phenol. In an embodiment, different R groups on the Si may be used to adjust the stability and/or the rate of the reaction with fluoride along with the water solubility of the silylated species which is likely less than that of the non-silylated species.

In an embodiment, a fluoride-deprotected phenolic species may be further reacted with a diazonium salt to produce an azo dye that yields a colorimetric response. In an embodiment, a diazonium salt may be selected to achieve a wavelength that may be easily detected and within range of a measuring apparatus or visually. The aqueous fluoride detection may be based on a rate of reaction of fluoride with the silane protected phenolic species and the rate of the subsequent coupling of the phenoxide with the diazonium salt. An amount of azo dye produced may be directly proportional to the concentration of fluoride in a solution.

In an embodiment, an O—Si bond is cleaved by fluoride. The resultant phenoxide species reacts with the diazonium salt coupling agent to produce a colored azo dye. The reaction of the O$^-$ (phenoxide) species with the diazonium salt yields a brightly colored compound that may be used as a colored species for measurement. The diazonium salt becomes a nitrogen double bond, forming an azo dye.

In an embodiment, naphthalene (denoted by a dotted ring), may be used to form a dye which may be red, yellow, or any color. In other embodiments, different compounds may be used to yield different colors of colorimetric or fluorometric dyes. In an embodiment, the colorimetric dye is unmasked for detection of fluoride in aqueous solution. In another embodiment, the dye itself is not added to the solution, but may be created as a result of the presence of fluoride. This may be advantageous because there is no free dye present in solution to yield an inaccurate reading of the concentration of aqueous fluoride. Any free dye in solution may result in a false higher reading of aqueous fluoride if the dye is not accounted for in a blank. In an embodiment, the masked dye results in a 1:1 ratio of dye molecule to fluoride due to fluoride cleavage of the O—Si bond. In an embodiment, an R or R' groups may be a combination of aryl or alkyl groups that create a sterically hinder environment around the O—Si bond. Possible sterically hindering groups may include: Alkyl chains of undefined lengths, ethoxy groups of undefined lengths, phenyl rings, tert-butyl groups, isopropyl groups, and the like. The R, R', and R" groups around the silicon do not have to be the same and may be a mixture. The R-groups are the sterically hindering groups, and the Si—Cl contains three sterically hindering groups.

In an embodiment, a colorimetric dye is not premade, instead the silane protecting group reacts with fluoride to generate a species that will later form a dye, and the dye may form in situ. In other words, there is no dye present in the aqueous solution until fluoride starts the reaction. Once fluoride reacts, a colorimetric dye may be created.

Referring to FIG. 6, in an embodiment, the synthesis of a protected phenol/naphthol and the subsequent reaction with a diazonium salt is illustrated. In an embodiment, the following synthesis scheme is used: a phenol or a naphthol (denoted with the dotted lines) is protected with a silane protecting group in the presence of a base in N,N'-dimethylformamide at room temperature. In FIG. 6 with respect to the test scheme: The silane protected phenol or naphthol can be reacted with an aqueous sample. Any fluoride present in solution will cleave the protecting group and regenerate the phenol or naphthol. Either of these species can go on to react with a diazonium salt in solution to produce a colored azo dye.

In an embodiment, the color may be a deep blue, or any color depending on whether a phenol or naphthol is used, or depending if the phenol or naphthol couples with a reagent at a later time to form an azo dye. In an embodiment, different R group may be used to adjust the color reported by the dye. In an embodiment, a red color is desired to achieve the greatest sensitivity to aqueous fluoride detection. Sensitivity may be a combination of the detection use model and the molecular extinction coefficient of the dye. A color or a shade of color may indicate the concentration of fluoride in the aqueous sample. For every one fluoride atom, one dye molecule is generated in a 1:1 ratio if the dye is mono protected. The amount of colored azo dye created is proportional to the amount of fluoride present in the aqueous solution. Accordingly, the absorbance of the azo dye can be measured to determine the amount of azo dye, which can be correlated to the amount of fluoride present in the sample. The relationship between the amount of azo dye and the amount of fluoride may be a linear relationship.

Embodiment 3

Figure 7:
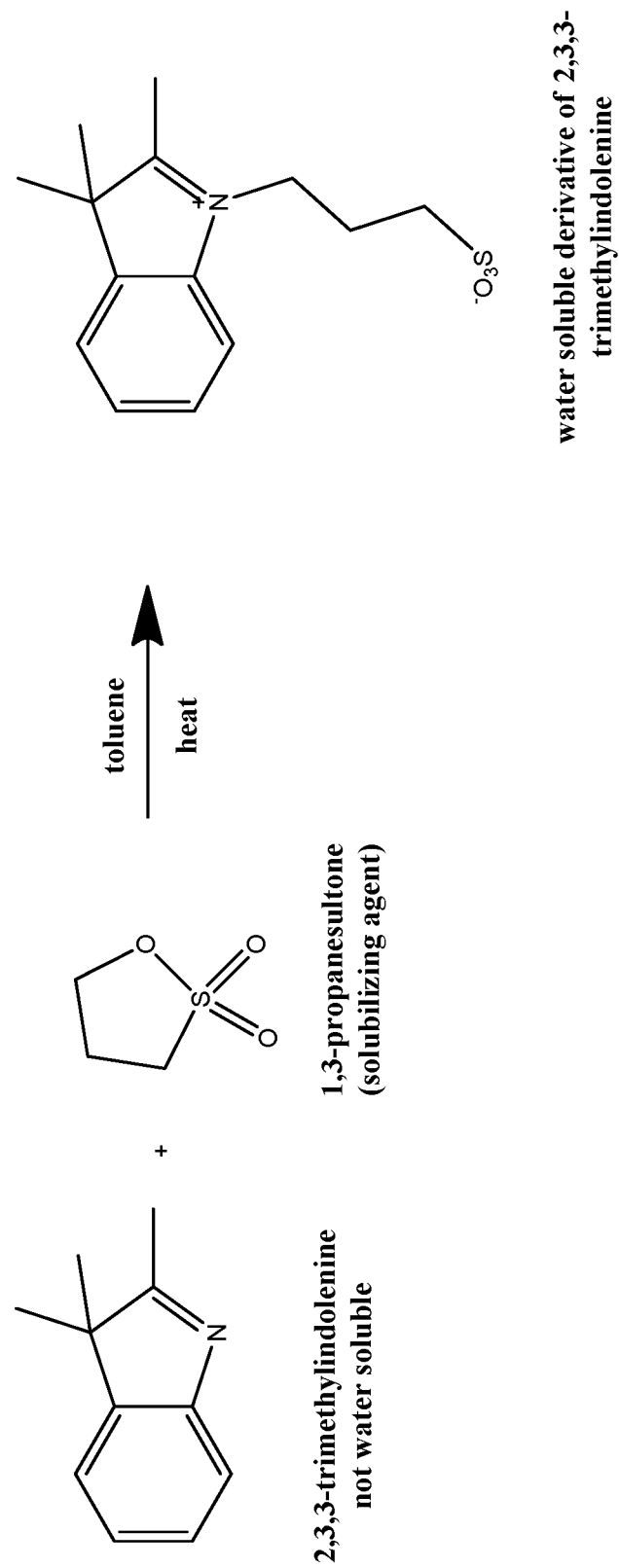
FIG. 7 illustrates a synthesis scheme of an embodiment.

Referring to FIG. 7, in an embodiment a water-soluble derivative of 2,3,3-trimethylindolenine may be generated. In an embodiment, 2,3,3-trimethylindolenine and 1,3-propanesultone may be combined in the presence of toluene and heat. The product in FIG. 7 may be used for the reaction described later in FIG. 9.

Figure 8:
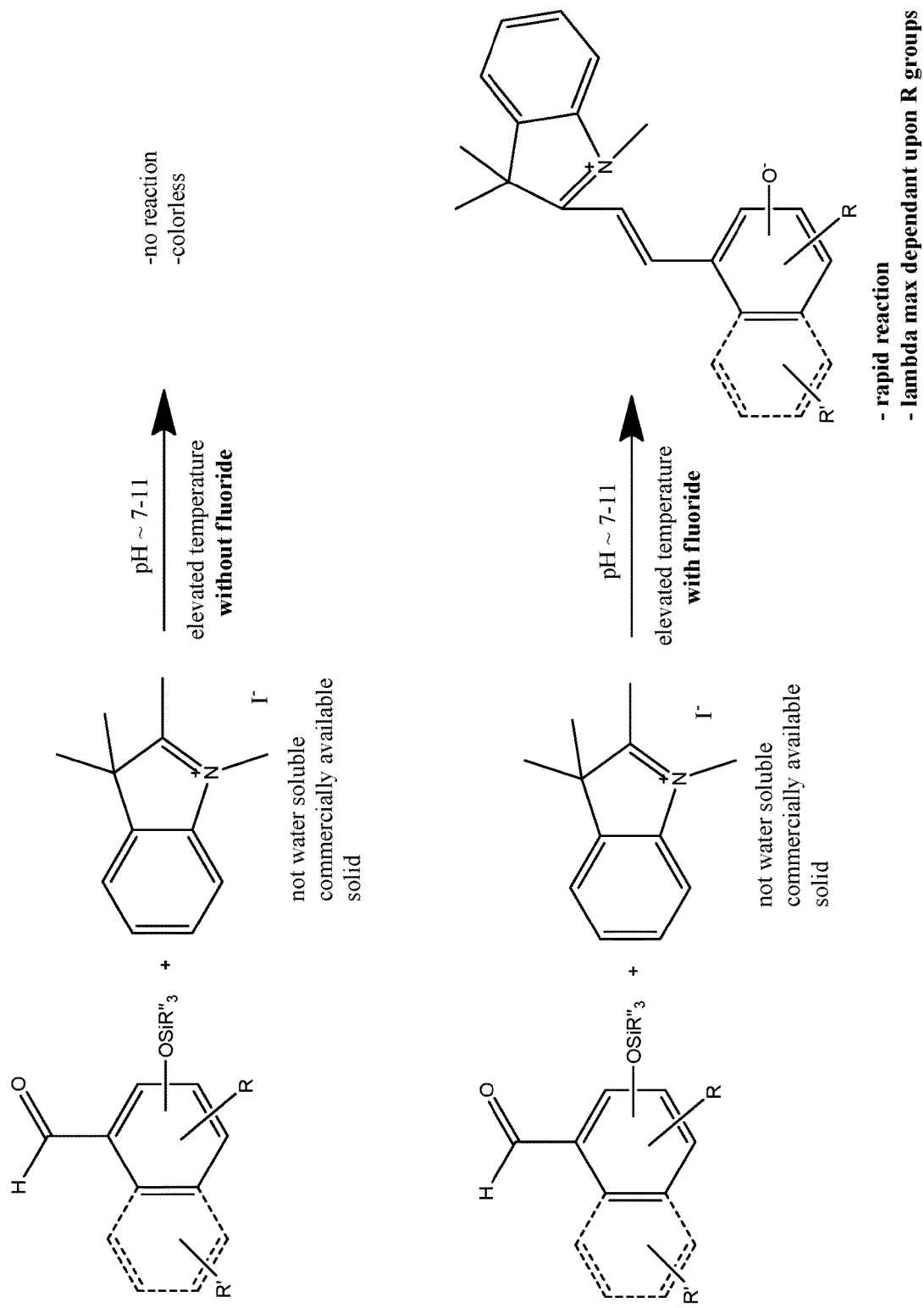
FIG. 8 illustrates a test scheme of an embodiment.

Referring to FIG. 8, in an embodiment, a silane protected phenol or naphthol species that contains a benzaldehyde functional group is reacted with 1,2,3,3-tetramethyl-3H-indolium iodide, in the presence of fluoride. In FIG. 8 Top Scheme illustrates the reaction in the absence of fluoride. Therefore, in the absence of fluoride, no reaction will occur between 1,2,3,3-tetramethyl-3H-indolium iodide and the silane protected derivative of the benzaldehyde. In FIG. 8 Bottom Scheme illustrates the reaction in the presence of fluoride. Therefore, in the presence of fluoride, the silane protected derivative of the benzaldehyde is deprotected and free to react with 1,2,3,3-tetramethyl-3H-indolium iodide to produce a hemicyanine.

In an embodiment, derivatives of the 2,3,3-trimethylindolenine species increases the water solubility of the material which in turn may increase the rate of reaction in aqueous solution at room and elevated temperatures.

Figure 9:
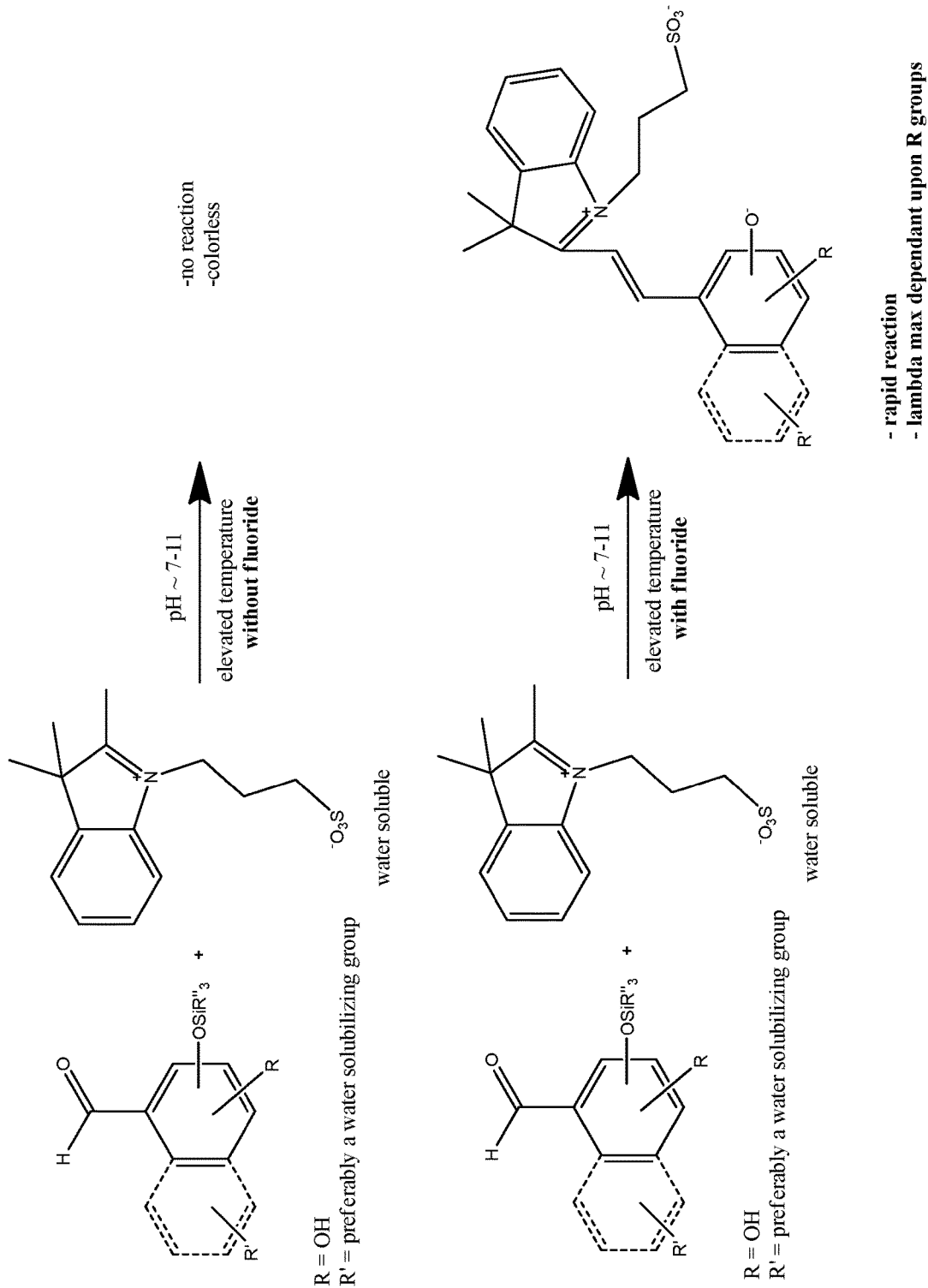
FIG. 9 illustrates a test scheme of an embodiment.

Referring to FIG. 9, a silane protected phenol or naphthol species that contains a benzaldehyde functional group is reacted with a water-soluble derivative of 2,3,3-trimethylindolenine, for example, the product of FIG. 7, in the presence of fluoride. The reaction requires the oxygen bound to the Si to be free, so that it may react with the 2,3,3-trimethylindolenine species. In the prescence of fluroide the O—Si bond is cleaved and form a new Si—F bond, the oxygen is free and creates a reaction which leads to color change. In FIG. 9, Top Scheme illustrates the reaction in the absence of fluoride. Therefore, in the absence of fluoride, no reaction will occur between the water-soluble derivative of 2,3,3-trimethylindolenine and the silane protected derivative of the benzaldehyde. In FIG. 9, Bottom Scheme illustrates the reaction in the presence of fluoride. Therefore, in the presence of fluoride, the silane protected derivative of the benzaldehyde is deprotected and free to react with the water-soluble derivative of 2,3,3-trimethylindolenine to produce a hemicyanine.

In an embodiment, a reaction may be heated to 50 degrees Celsius, or may be at ambient temperature. Heating the reaction may decrease the time to reach normalcy or completion of the reaction. For example at 50 degrees Celsius, the reaction occurs within an order of minutes. In an embodiment, the measuring equipment, such as a spectrophotometer, may provide a constant temperature to maximize the reaction. Reactions at cooler temperatures achieve a desired result, but may take a longer period of time.

Figure 10:
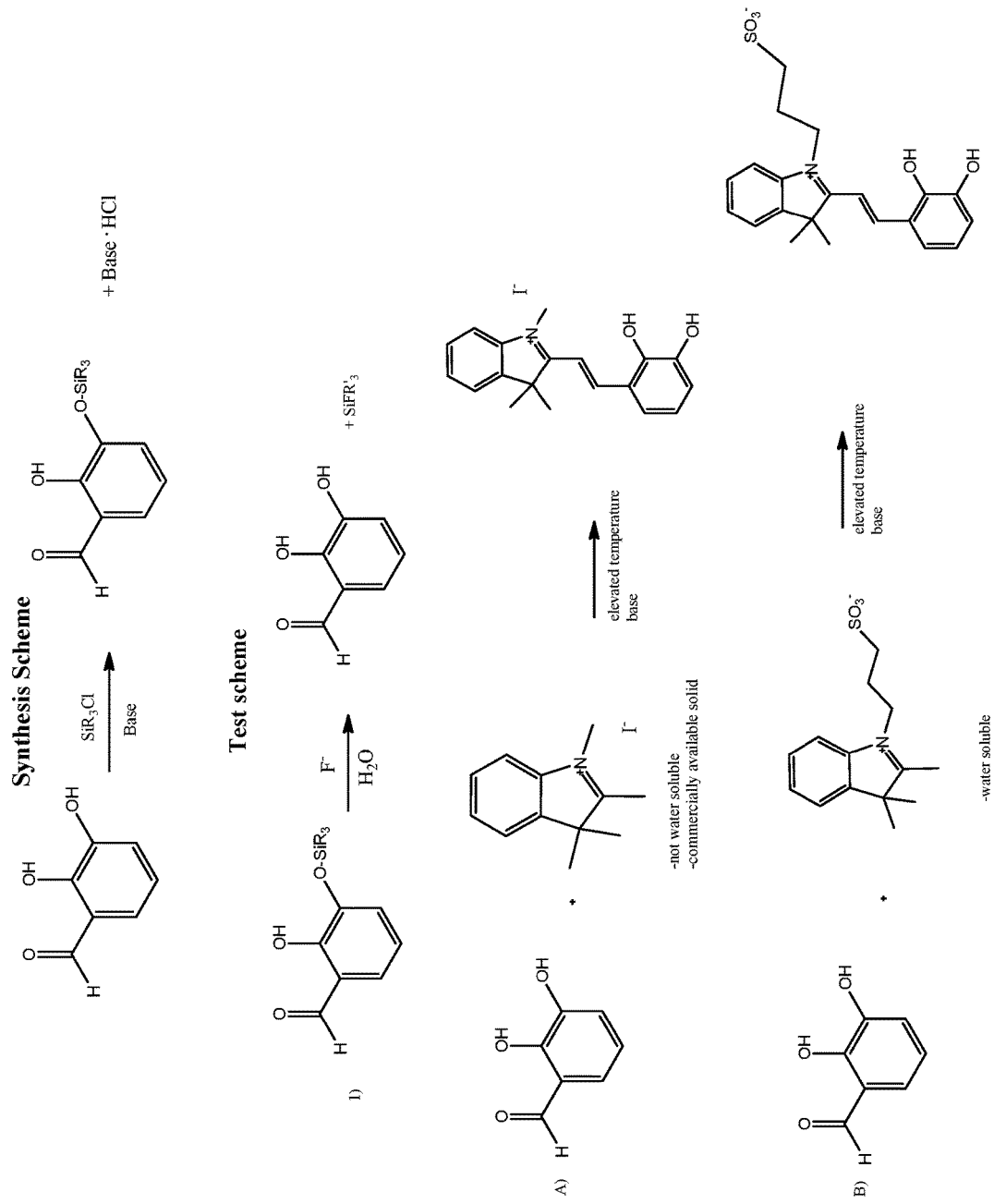
FIG. 10 illustrates an example embodiment of a general synthesis scheme for protection of a catechol and test scheme for hemicyanine synthesis.

FIG. 10 illustrates an example embodiment of a general reaction scheme for protection of a catechol and test scheme for hemicyanine synthesis. The catechol containing a benzaldehyde group would react with a silane protecting group similar to the synthesis scheme in FIG. 6. In an aqueous solution containing fluoride, the fluoride will deprotect the mono-protected catechol to regenerate the original catechol that contains a benzaldehyde group. The deprotected species can be reacted with a commercially available non-water-soluble derivative of the 2,3,3-indolenine species to form a water soluble hemicyanine (A). Alternatively, it can be reacted with a water-soluble derivative of 2,3,3-trimethylindolenine to form a water soluble hemicyanine (B). The hemicyanine product for reaction (A) or (B) is brightly colored and the absorbance is directly proportional to the amount of fluoride in solution.

The amount of colored hemicyanine created is proportional to the amount of fluoride present in the aqueous solution. Accordingly, the absorbance of the hemicyanine can be measured to determine the amount of hemicyanine, which can be correlated to the amount of fluoride present in the sample. The relationship between the amount of hemicyanine and the amount of fluoride may be a linear relationship.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for preparing a fluoride sensitive species in an aqueous solution, comprising:
   causing a polyethylene glycol (PEG) monomethyl ether to produce an ester;
   reacting the ester in ammoniated tetrahydrofuran to produce an amino polyethylene glycol;
   placing, in a solution comprising a benzaldehyde species with a phenol functional group and a carboxylic acid functional group, a 1,2,3,3 3H-indolium iodide to produce a hemicyanine comprising a phenol functional group and a carboxylic acid functional group;
   combining, in a polar aprotic solvent, the hemicyanine comprising the phenol functional group and the carboxylic acid functional group with a 1,1-carbonyldiimidazole (CDI) and adding the amino-PEG to produce a hemicyanine-PEG comprising a phenol functional group; and
   creating a fluoride sensitive hemicyanine species containing a protecting group by reacting the hemicyanine-PEG comprising the phenol functional group with a $SiR_3$ species, wherein the $R_3$ is selected from the group consisting of: an alkyl chain of undefined length, an ethoxy group of undefined length, a phenyl ring, a tert-butyl group and an isopropyl group.

2. The method of claim 1, wherein the polyethylene glycol (PEG) monomethyl ether reaction comprises a mesyl chloride, a triethylamine, a dichloromethane, and a tetrahydrofuran.

3. The method of claim 1, wherein the reaction of the hemicyanine-PEG with a $SiR_3$ species generates a silane protecting group on a phenol produced by a reaction of the phenol functional group of the hemicyanine-PEG and the $SiR_3$ species.

4. The method of claim 1, wherein the ester is selected from the group consisting of: a mesylate and a tosylate.

5. The method of claim 1, wherein the protecting group is a silane protecting group.

6. The method of claim 5, wherein the silane protecting group of the fluoride sensitive hemicyanine species becomes deprotonated when contacted with fluoride in an aqueous solution.

7. The method of claim 1, wherein a reaction of the benzaldehyde and the 1,2,3,3 3H-indolium iodide comprises piperidine and ethanol.

8. The method of claim 1, wherein the hemicyanine comprises a colorimetric species.

9. The method of claim 8, further comprising combining the fluoride-sensitive hemicyanine species with an aqueous solution and measuring an amount of the hemicyanine species, wherein the amount of the hemicyanine species is proportional to an amount of fluoride in the aqueous solution.

* * * * *